(12) United States Patent
Gribb et al.

(10) Patent No.: US 10,300,237 B2
(45) Date of Patent: May 28, 2019

(54) MEDICAL CARBON MONOXIDE DELIVERY SYSTEM

(71) Applicant: Wisconsin Alumni Research Foundation, Madison, WI (US)

(72) Inventors: Tye Travis Gribb, Madison, WI (US); Duncan Bathe, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 150 days.

(21) Appl. No.: 15/431,086

(22) Filed: Feb. 13, 2017

(65) Prior Publication Data

US 2017/0165446 A1 Jun. 15, 2017

Related U.S. Application Data

(62) Division of application No. 13/771,273, filed on Feb. 20, 2013, now Pat. No. 9,604,026.

(51) Int. Cl.
*A01N 1/02* (2006.01)
*A61M 16/10* (2006.01)
(Continued)

(52) U.S. Cl.
CPC .......... *A61M 16/109* (2014.02); *A01N 1/021* (2013.01); *A01N 1/0247* (2013.01); *A01N 1/0273* (2013.01); *A61M 11/041* (2013.01); *A61M 11/042* (2014.02); *A61M 16/0066* (2013.01); *A61M 16/0087* (2013.01); *A61M 16/0666* (2013.01); *A61M 16/10* (2013.01); *A61M 16/1005* (2014.02); *A61M 16/105* (2013.01); *A61M 16/0069* (2014.02); *A61M 16/0093* (2014.02); *A61M 16/06* (2013.01); *A61M 16/0672* (2014.02); *A61M 2016/0039* (2013.01); *A61M 2016/1035* (2013.01); *A61M 2202/0233* (2013.01); *A61M 2205/123* (2013.01); *A61M 2205/127* (2013.01); *A61M 2205/273* (2013.01); *A61M 2205/3368* (2013.01); *A61M 2205/368* (2013.01); *A61M 2205/3633* (2013.01); *A61M 2205/3653* (2013.01); *A61M 2205/502* (2013.01); *A61M 2205/52* (2013.01); *A61M 2205/6018* (2013.01); *A61M 2205/6054* (2013.01); *A61M 2205/6072* (2013.01); *A61M 2205/7545* (2013.01); *A61M 2205/8206* (2013.01)

(58) Field of Classification Search
CPC ..... A01N 1/021; A01N 1/0247; A01N 1/0273
See application file for complete search history.

(56) References Cited

U.S. PATENT DOCUMENTS 5,681,285 A * 10/1997 Ford ...................... A61M 5/172
604/151
7,252,806 B1 * 8/2007 Merritt .................. B01D 53/62
422/168

(Continued)

*Primary Examiner* — William H. Beisner
(74) *Attorney, Agent, or Firm* — Boyle Fredrickson S.C.

(57) ABSTRACT

A medical carbon monoxide generator provides for a solid carbon material that may be heated at substantially normal atmospheric pressure to provide a source of medical quality carbon monoxide. The heating source may be an electrical filament or laser controllable by a microcontroller to provide accurate delivery rates and amounts. In one embodiment, a replaceable cartridge holding the carbon material may be used.

16 Claims, 4 Drawing Sheets

(51) Int. Cl.
*A61M 11/04* (2006.01)
*A61M 16/00* (2006.01)
*A61M 16/06* (2006.01)

(56) References Cited

U.S. PATENT DOCUMENTS

| | | | | |
|---|---|---|---|---|
| 8,091,549 B2* | 1/2012 | Montgomery | ... | A61M 16/0051 128/204.21 |
| 2003/0150451 A1* | 8/2003 | Shayan | ... | A61M 11/041 128/203.12 |
| 2009/0311165 A1* | 12/2009 | Podgorney | ... | G01N 33/0006 423/418.2 |
| 2010/0012117 A1* | 1/2010 | Krebs | ... | A61M 16/10 128/203.14 |
| 2010/0074911 A1* | 3/2010 | Cutts | ... | A61M 11/005 424/184.1 |
| 2012/0178150 A1* | 7/2012 | Tempelman | ... | A01N 1/0226 435/286.1 |

* cited by examiner

MEDICAL CARBON MONOXIDE DELIVERY SYSTEM

CROSS REFERENCE TO RELATED APPLICATION

This application is a divisional application of U.S. patent application Ser. No. 13/771,273 filed Feb. 20, 2013 and hereby incorporated by reference.

STATEMENT REGARDING FEDERALLY SPONSORED RESEARCH OR DEVELOPMENT

BACKGROUND OF THE INVENTION

The present invention relates to medical gas generators and in particular to a device for producing medical purity carbon monoxide for therapeutic purposes.

Carbon monoxide is a colorless and odorless gas that is frequently a byproduct of combustion and which can be toxic to humans in high concentrations. In lower concentrations, however, recent research has suggested that carbon monoxide can have efficiency in bio protective and anti-inflammatory applications. In such situations, low concentrations of carbon monoxide may provide therapies for cardiovascular disease and cancer treatment, aid in organ preservation and in preventing acute and chronic rejection of transplanted organs, and may help in the treatment of acute lung and kidney injury or in cases of sepsis and shock.

Medical grade carbon monoxide is available in pressurized cylinders from medical gas providers. Carbon monoxide is an odorless and colorless toxic and flammable gas. Pressurized cylinders are naturally heavy and difficult to manage. All pressurized cylinders possess inherent and unavoidable safety issues including the risk of asphyxiation and of explosive rupture of the tank. The toxic and flammable properties of carbon monoxide engenders additional risk as even a relatively slow, and difficult to detect, leak could have catastrophic consequences in an uncontrolled environment. These risks lead to a general desire to minimize the presence of pressurized cylinders, particularly of toxic and flammable gases, in many situations including public transport, all flying vehicles (airplanes and helicopters), and in-home care. This presents a significant problem in the use of carbon monoxide for many of the possible indications including organ preservation, at least to the extent that such organs are often transported in a helicopters and other aircraft on a rush basis.

SUMMARY OF THE INVENTION

The present invention provides a carbon monoxide generator for medical use that operates substantially at standard atmospheric pressure. The generator produces carbon monoxide from a solid carbon source that is heated on demand to specific temperatures to generate a desired carbon monoxide stream. A control system provides both versatile delivery and monitoring of the stream for safety. Eliminating the need for a pressurized bottle of carbon monoxide allows the generator to be portable and generally allowable in many situations in which pressurized cylinders are problematic Specifically then, in one embodiment, the invention provides a medical carbon monoxide generator having a reaction chamber holding a purified carbon element and providing an ingress port and egress port. A pump communicates with the ingress port to provide a source of air passing into the reaction chamber and out of the egress port and within the reaction chamber an electrically controllable heater element heats the purified carbon element in the presence of the air to generate carbon monoxide gas from the reaction of the heated purified carbon with the air of the reaction chamber. A sensor system monitors carbon monoxide passing out the egress port and provides a signal to an electronic controller to control the electrically controllable heater in response thereto. The carbon monoxide is delivered to a respiratory delivery appliance through the egress port to provide carbon monoxide to a patient for respiration thereof.

It is thus a feature of at least one embodiment of the invention to provide a convenient source of medical carbon monoxide eliminating the need for pressurized gas bottles.

The purified carbon element may be at least USP grade pure carbon and may be of a limited volume to prevent generation of enough carbon monoxide to present either a toxicological or flammability risk in even a relatively small enclosure.

It is thus a feature of at least one embodiment of the invention to provide medically pure carbon monoxide by employing a pure solid carbon precursor eliminating the need for substantial filtration or purification of the resulting gas flow.

The sensor system may include a flow sensor measuring flow from the egress port and at least one carbon monoxide concentration sensor.

It is thus a feature of at least one embodiment of the invention to provide close loop control for precise and accurate delivery of a potentially toxic gas.

The electronic controller may control the electrically controllable heater element to provide a predetermined time varying change in carbon monoxide delivered to the respiratory delivery appliance.

It is thus a feature of at least one embodiment of the invention to permit complex treatment schedules without the need for high pressure metering valves or the like or a venting of excess carbon monoxide.

The electrically controllable heater element may be an ohmic resistor in thermal communication with the purified carbon element.

It is thus a feature of at least one embodiment of the invention to provide a simple and low-cost method of generating carbon monoxide in controlled quantities.

Alternatively, the electrically controllable heater element may be an optical radiation source focused on the purified carbon element, for example, a laser.

It is thus a feature of at least one embodiment of the invention to provide for extremely high-speed temperature control possible with localized optical heating for precise carbon monoxide metering.

The sensor system may include redundant carbon monoxide sensors and the electronic controller may use readings from the carbon monoxide sensors to deduce carbon monoxide concentration in the egress port.

It is thus a feature of at least one embodiment of the invention to provide for a high degree of safety commensurate with possible toxicity and flammability of carbon monoxide.

The electronic controller may record a time record of carbon monoxide delivery through the egress port.

It is thus a feature of at least one embodiment of the invention to provide for precise record-keeping of the treatment for verification of the treatment plan and monitoring proper operation of the generator.

The electronic controller may determine a total amount of carbon monoxide generated in the reaction chamber during operation of the medical carbon monoxide generator.

It is thus a feature of at least one embodiment of the invention to permit treatment monitoring and control according to total carbon monoxide delivery.

The reaction chamber may be in a cartridge releasably connectable to at least one of the fan and sensor system.

It is thus a feature of at least one embodiment of the invention to provide a convenient method of replacing the carbon source for reliable and consistent behavior.

It is thus a feature of at least one embodiment that the carbon source be of limited volume such that a "worst case scenario" cannot generate enough carbon monoxide to create a hazard in most environments.

The cartridge may include a data communication element communicating with a remainder of the medical carbon monoxide generator system to identify the cartridge for controlling operation of the medical carbon monoxide generator.

It is thus a feature of at least one embodiment of the invention to permit treatment protocols to be implemented by selection of the proper cartridge without the need for complex programming of the generator by the user.

The electronic controller may control the electric heater according to the identification of the cartridge to provide at least one of a predetermined schedule of carbon monoxide delivery from the cartridge and a predetermined total production of carbon monoxide from the cartridge.

It is thus a feature of at least one embodiment of the invention to ensure proper operation of the cartridge by monitoring its use and possible exhaustion.

The data communication element may include a memory for storing usage data with respect to the reaction chamber.

It is thus a feature of at least one embodiment of the invention to ensure spent cartridges are not reused regardless of the device with which they are associated.

The medical carbon monoxide generator may further include a filter filtering the air received by the fan.

It is thus a feature of at least one embodiment of the invention to provide a system that may work with atmospheric pressure air from the room or the like.

One embodiment the invention may provide an organ transplant container system having an insulated container for receiving a transplant organ held in a storage liquid and a carbon monoxide generator attached to the insulated container and communicating with the storage liquid to provide a source of carbon monoxide to the storage liquid by heating a carbon source in atmospheric air.

It is thus a feature of at least one embodiment of the invention to provide a system for preserving transplant organs during transportation compatible with high-speed air transport by helicopter or the like.

The organ transplant container may include a scrubber element communicating with the storage liquid to vent gas from the storage liquid into the scrubber element and to scrub carbon monoxide from the vented gas.

It is thus a feature of at least one embodiment of the invention to provide a system that may be used in a closed environment such as a cockpit without concern about excess carbon monoxide levels accumulating.

These particular features and advantages may apply to only some embodiments falling within the claims and thus do not define the scope of the invention.

DETAILED DESCRIPTION OF THE PREFERRED EMBODIMENT

Figure 1:
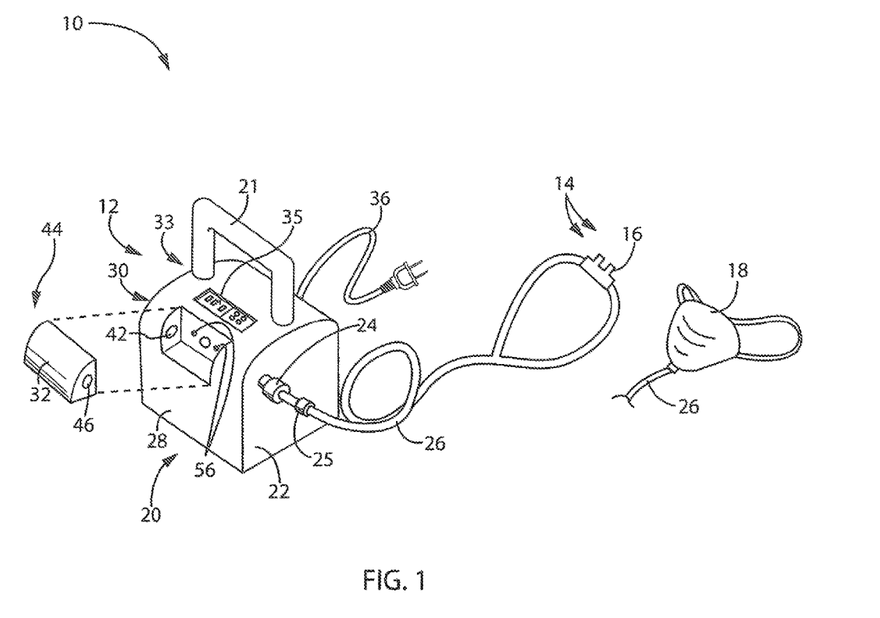
FIG. 1 is a perspective view of a first embodiment of the carbon monoxide generator of the present invention as may be used with a respiratory appliance for delivery of carbon monoxide to a patient's respiratory tract.

Referring now to FIG. 1, a medical carbon monoxide generator system 10, may include a generator unit 12 communicating with a delivery appliance 14 such as a nasal cannula 16 or a face mask 18 of a type that may deliver gases to a patient's respiratory tract such as are generally understood in the art.

The generator unit 12 may be a portable device having a housing 20 transported by use of the handle 21 or the like extending upward from the housing 20. One sidewall 22 of the housing 20 may provide for a releasable tubing connector 24 for attachment to flexible tubing 26 of the delivery appliance 14 (the latter of which may be disposable) and in particular for communicating with flexible tubing 26 leading to either the nasal cannula 16 or the face mask 18.

A front wall 28 of the housing 20 may provide for a socket 30 that may receive a replaceable cartridge 32 as will be described in further detail below as held by mechanical snap elements or the like. An upper surface 33 of the housing 20 may provide for a user interface 35, for example, including an LCD display and membrane or other type pushbuttons for user control of the medical carbon monoxide generator system 10. Power for the generator system 10 may be provided, for example, by a line cord 36 or by internal battery systems, or both.

Figure 2:
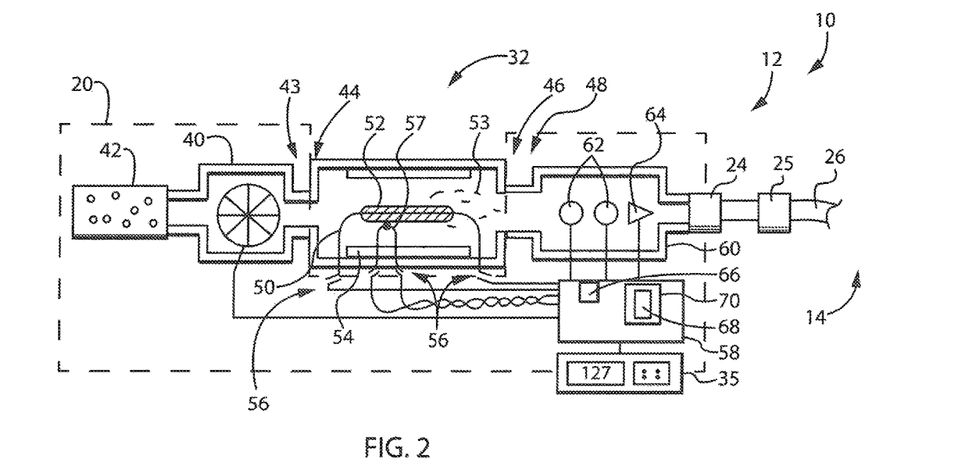
FIG. 2 is a block diagram of the generator of FIG. 1 showing a cartridge based filament system in which an electrical filament is heated in the proximity of purified carbon to generate carbon monoxide in the control loop as controlled by sensors.

Referring now also to FIG. 2 the generator unit 12 may incorporate an electric fan 40 or similar blower or pump receiving air from an air filter 42, for example a HEPA filter suitable for removing dust, mold and allergens from room air. The air filter 42 may further include activated carbon filtration or the like for odor and volatile reductions. Generally, the generator unit 12 may thus operate at standard atmospheric pressures with standard room air without the need for bottled or compressed gas. An outlet of the fan 40 may pass to a port 43 in the side of the socket 30 that may engage with the corresponding port 44 in one side of the cartridge 32 when the cartridge 32 is in place within the socket 30. An air stream from the fan 40 through port 43 and port 44 may pass through the cartridge 32 to an exit port 46 in the cartridge 32 that connects to port 48 of the generator unit 12 when the cartridge 32 is in the socket 30. One or both of the ports 44 and 46 operate in conjunction with the fan 40 to limit the oxygen in the cartridge 32 favoring the production of CO over $CO_2$.

A resistive filament 50 may be positioned in the air stream within the cartridge 32, and may be coated with or proximate to a purified carbon material 52, for example, having a USP medical grade meeting or exceeding requirements of the US Pharmacopeia. In one embodiment, this purified carbon material 52 may be elemental carbon or elemental carbon compounded with a binder material with low volatility and reactivity. The resistive filament 50 provides ohmic resistance to produce a desired and predetermined heating as a function of current introduced through the resistive filament 50 as may be controlled, for example, by a controlled current source of a type known in the art. Desirably, the resistive filament 50 is operated to provide temperatures of 600 C or more that favor CO production in a limited oxygen environment enforced by the operation of the fan 40.

Generally, the amount of purified carbon material 52 may be limited to approximately an amount needed for a particular medical procedure and the cartridges 32 may be identified to a particular medical procedure in this regard as will be discussed below. The resistive filament 50 may extend longitudinally along the axis of airflow within insulating walls 54 sized to allow airflow outside of the carbon material 52 within the walls 54. Ends of the resistive filament 50 may communicate by releasable electrical connectors 56 to a controller 58 within the housing 20 of the generator unit 12. A thermal sensor 57 may also be attached to the carbon material 52 to provide a reading of temperature of the carbon material 52 during heating and may communicate through similar connectors 56 with the controller 58.

As will be discussed in greater detail below, an electrical current produced and controlled by the controller 58 may heat the filament 50 to cause heating of the carbon material 52 to a degree as to generate carbon monoxide 53 in reaction with oxygen in the air passing over the filament. In this regard, the cartridge 32 provides a replaceable reaction chamber for generating carbon monoxide.

Carbon monoxide gas exiting port 46 through port 48 may pass into a sensor chamber 60 holding redundant carbon monoxide sensors 62 and a flow sensor 64. The sensor chamber 60 connects at an outlet to connector 24 communicating with tubing 26 of appliance 14. Each of the carbon monoxide sensors 62 and flow sensor 64 may provide an input signal to the controller 58 and the controller 58 may provide an output signal controlling the fan 40. In this way, the controller 58 may effect a closed-loop control algorithm to control the concentration and total volume of carbon monoxide delivered into the appliance 14 in accordance with control signals received from the control interface 35 and may confirm operation on the same control interface 35. A delivery concentration (mg CO/hour) may be entered into the control interface 35 or a concentration per body weight per hour and body weight entered into the control interface 35. In this latter case, the entered value may be compared against a safe maximum of 3 mg of CO per kg of patient body weight per hour to provide an override or alarm, if necessary.

In one embodiment, a cleanup filter 25 may be placed in series with the tubing 26 to the appliance 14, providing a filtration of particulate matter and possibly a chemical filter to remove undesired combustion byproducts such as nitrogen oxides or volatile materials.

For purposes of control, the controller 58 may generally include a computer processor 66 executing a stored program 68 held in memory 70. The stored program 68 may provide, for example, one or more schedules of carbon monoxide delivery (as will be discussed below) noting a series of concentrations and durations over time as implemented by an internal clock of the processor 66. The concentrations of the schedules may be implemented by control of the fan 40 and/or current to the filament 50 according to feedback signals received from the thermal sensor 57, the carbon monoxide sensors 62 and the flow sensor 64 using standard feedback techniques, for example, by implementing one or more PID type algorithms, for example, operating temperature control loops and flow control loops. The scheduling process will be described in greater detail below.

Figure 3:
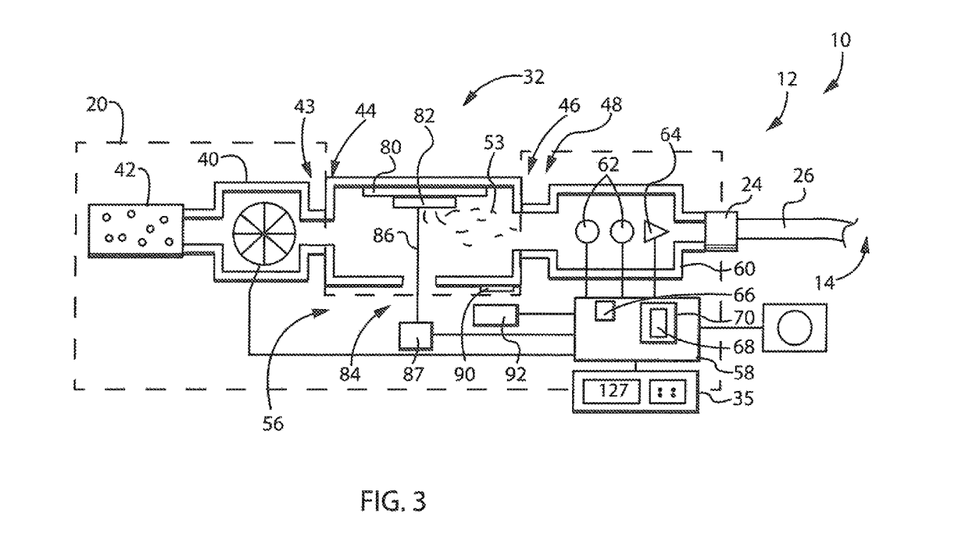
FIG. 3 is a figure similar to that of FIG. 2 showing an alternative cartridge design employing a laser for heating of the carbon material to produce carbon monoxide.

Referring now to FIG. 3, in an alternative embodiment of the cartridge 32, the cartridge 32 may provide for an insulating support 80 within the cartridge 32 supporting a purified carbon sheet 82 (of similar carbon material 52 described above) opposite an optical port 84 along an axis 86 generally perpendicular to the flow of air within the cartridge 32 between ports 44 and 46. A solid-state laser 87 positioned within the housing 20 may direct a beam of light along axis 86 to provide intense surface heating of the carbon sheet 82 producing a stream of carbon monoxide 53 to be controlled and conducted to the appliance 14 in the manner described above with respect to the filament 50. In one embodiment, a mechanism to scan the laser beam with respect to the carbon sheet 82 may be provided to ensure a fresh surface. Accurate control of the amount of carbon monoxide 53 generated may be provided by the duty cycle modulation of the laser 87 as part of a control feedback loop in conjunction with the sensors and fan described above, however, in this case with the controller 58 controlling operation of the laser 87 as opposed to current flow through a filament. The laser desirably operates to rapidly elevate the carbon sheet 82 to above 600 C in a small area that will be oxygen limited.

In both of the embodiments described with respect to FIG. 2 and FIG. 3, the cartridge 32 may provide for an identifying tag 90 such as an RFID tag or barcode or the like that may be read by a reader 92 held within the housing 20 adjacent to the tag 90 when the cartridge 32 is within the socket 30. This identifying tag 90 may be "read-only" (as with the example of a barcode) or may provide for limited writable data storage. In both cases, the tag 90 may uniquely identify the cartridge 32, for example with a serial number, and may identify the cartridge 32 to a particular medical procedure, for example, appropriate for the amount of carbon material within the cartridge. This latter information may be used to guide the protocol implemented by the controller 58 by a connection between the reader 92 and the controller 58. In one example, this information may provide a particular schedule for the delivery of carbon monoxide including concentrations with respect to time (e.g. CO mg/kg of patient weight/hr or CO mg/hr) or total delivery (e.g. 100 mg for a single use cartridge intended for use for an hour or 1-2 grams for a multi use cartridge). It will, be understood that the necessary information for this purpose may be stored directly on the tag 90 or the tag may provide an index to a separate storage of this information in the memory 70 of the controller 58. Use of the cartridge 32 to effectively program the generator unit 12, eliminates the need for complex programming of the generator unit 12, for example, through the user interface 35. In the case where the tag 90 may receive and store data, stored data may be used to designate a rated life of the cartridge that remains and prevent inadvertent reuse of spent cartridges 32. In one system, the remaining life of the cartridge 32 may be stored on the tag 90. Alternatively the remaining life may be stored in memory 70 linked to a unique serial number of a cartridge 32 provided by tag 90, and the remaining life may be checked prior to use of a cartridge 32.

In some embodiments, the controller 58 may communicate with the data recorder device 96, for example a thermal printer, that may log measurements made by the carbon monoxide sensors 62 and flow sensor 64 to confirm a particular medical treatment. The data recorder device 96 may alternatively be a memory storage device such as a flash memory or other memory type and may communicate with the controller 58 either by direct electrical connection through a connector or wirelessly or the like as is understood in the art.

In an alternative embodiment, the cartridges 32 may be designed to operate open loop using a known strength of the laser 87 or electrical current provided to the filament 50 and known restricted airflow control by the fan 42 to favor the production of CO over $CO_2$. To the extent that this open loop preference can only be ensured for limited period of time (for example with a pristine carbon source receiving the laser beam 86 or operation with, a relatively fresh coating of carbon material 52 on the filament 50) the cartridge 32 may be programmed to require replacement by the operator after this period of time has been exhausted before the carbon source is exhausted.

Figure 4:
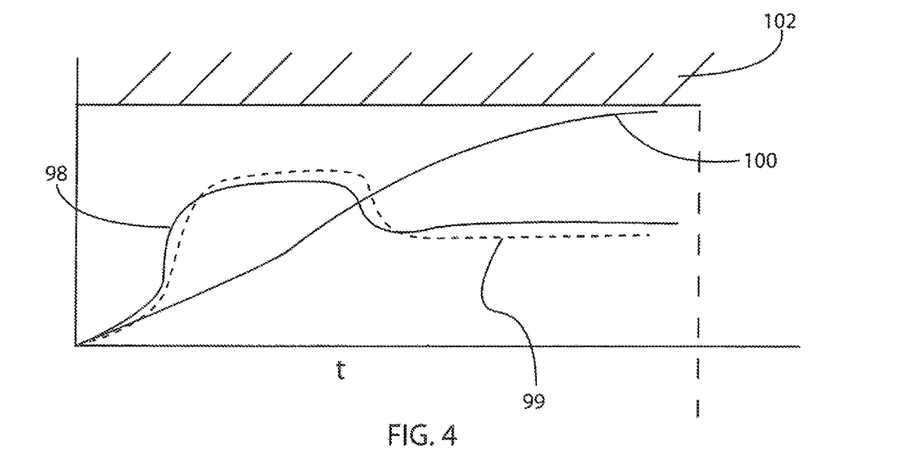
FIG. 4 is a chart showing an example predetermined delivery schedule that may be implemented with the present invention together with monitoring data that may be logged and tracked for safety purposes.

Referring now to FIG. 4, the generator unit 12 may operate to implement a stored protocol 98 providing a schedule of carbon monoxide delivery (for example concentration and/or flow rate delivered to the appliance 14) as a function to time. For example, as depicted, an initial high concentration amount may be delivered followed by a lower steady state concentration amount ultimately terminating at a predetermined time. The depicted schedule assumes a constant flow rate; however, this is not required. Delivery may begin when the generator unit 12 is activated by a user through the user interface 35 and may proceed as monitored by the sensors 62 and 74. In one embodiment, readings from the sensors 62 are compared and averaged so long as the difference between the carbon monoxide sensors 62 is less than a predetermined threshold amount. A difference beyond this threshold amount, such as may indicate a failure of a carbon monoxide sensor 62, may stop operation of the generator of unit 12 in production of carbon monoxide and provide an alarm to the user through user interface 35. In such cases, fan 40 may remain on to provide a purging of excess carbon monoxide from the appliance 14. Audible or visual alarms may then be provided on the user interface 35 and alarm signals may be transmitted, for example, wirelessly to remote monitoring devices.

The readings of the carbon monoxide sensors 62 and flow sensor 64 may be tracked and stored to provide actual delivery schedule 99 which will generally conform closely to the stored protocol 98 or the close loop control affected by the controller 58. Deviation between these two curves of actual delivery schedule 99 and a stored protocol 98 may be used to provide for an alarm condition indicating possible equipment malfunction, again through user interface 35, and again may stop generation of carbon monoxide. The information of delivery schedule 99 may be provided to the data recorder device 96 as discussed above or recording.

Total carbon monoxide delivery 100 may also be tracked by calculating the integral of the actual delivery schedule 99 weighted by a flow rate from flow sensor 64. This total carbon monoxide delivery 100 may be used to determine the lifetime of the cartridge 32. Alternatively, a simply lapsed time of use of the cartridge 32 may be employed. Either the actual delivery schedule 99 or total carbon monoxide delivery 100 may be compared against an alarm limit 102 to provide an indication of possible problems with the delivery procedure that may trigger a shutdown of the generator unit 12 and suitable alarms.

Figure 5:
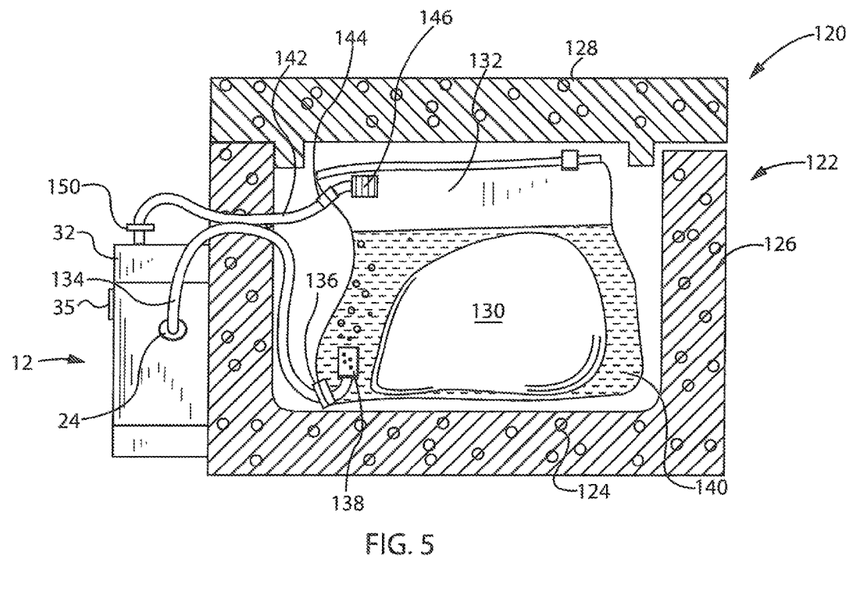
FIG. 5 is a cross-sectional view of an organ transplant container employing the medical carbon monoxide generator of the present invention providing both a source of carbon monoxide to an organ pouch and the scrubbing of excess carbon monoxide recovered from that pouch.
Figure 6:
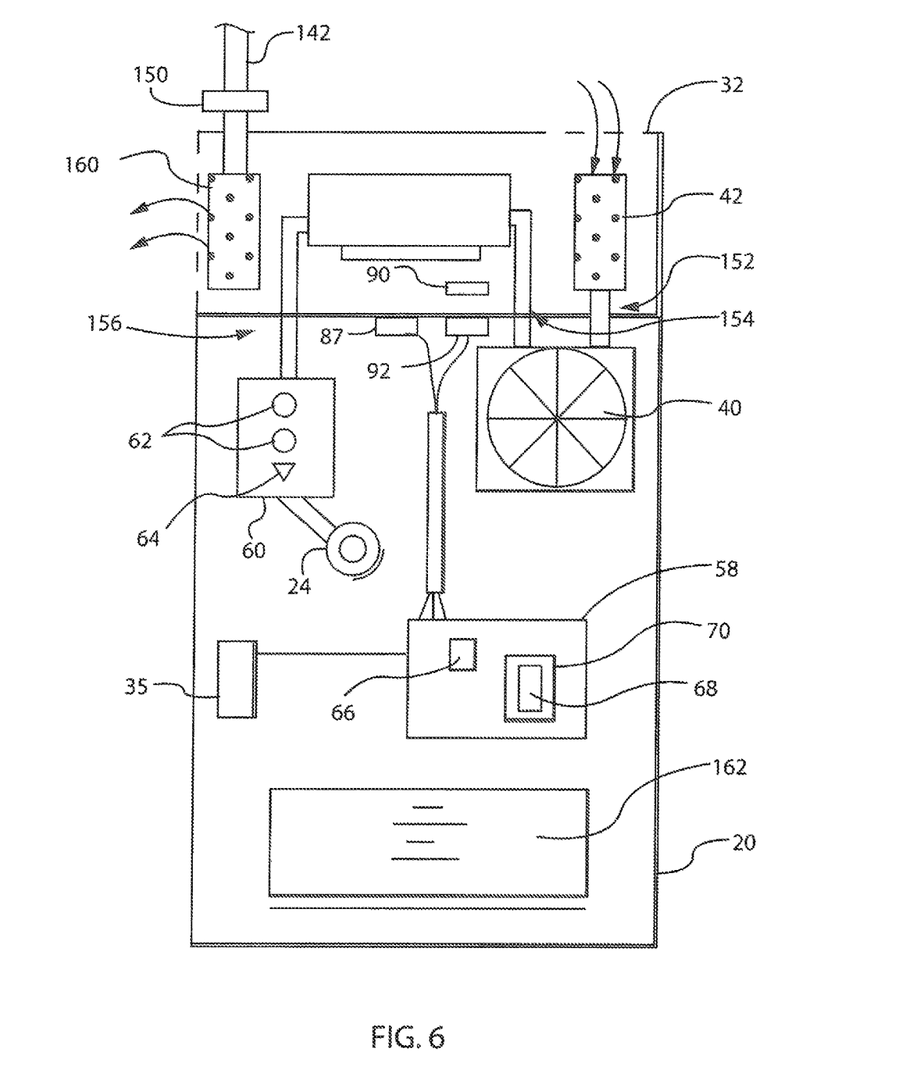
FIG. 6 is a block diagram of the generator of FIG. 5 showing the various components thereof.

Referring now to FIGS. 5 and 6, in an alternate embodiment, the generator unit 12 part of an organ carrier system 120 may provide, for example, an insulated watertight container 122 having a base wall 124 and upstanding sidewalls 126 constructed of expanded polymer foam within a plastic shell. An insulated lid 128 may attach at the top of the upstanding sidewalls 126 to provide an enclosed insulated volume that may receive a transplant organ 130, for example, sealed in a plastic pouch 132 together with a preservation fluid 140 of a type known in the art and typically selected for the type of organ. The generator unit 12 may attach to one upstanding sidewall 126 and connector 24 of the generator unit 12 may attach to a carbon monoxide delivery line 134 threaded out of an opening in the sidewall 126 from the pouch 132. At the pouch 132, the delivery line 134 may be welded to a pass-through flange 136 of the pouch 132 to provide a conduit into the pouch 132 leading to a diffusion element 138 providing for a of bubbling carbon monoxide 53 through a transplant organ preservation fluid 140 during transport of the organ 130. A monoxide return line 142 may attach to a similar pass-through flange 144 positioned near the top of the pouch 132 and attached within the pouch 132 to a liquid filter 146 resisting in flow of liquid to return excess gaseous carbon monoxide to the generator unit 12 at a connector 150 on cartridge 32.

Referring specifically to FIG. 6, cartridge 32, in this embodiment, may incorporate the intake filter 42 described above. The intake filter 42 provides input air through a port interface 152 between the cartridge 32 and the housing 20 as drawn by the fan 40. Fan 40, in turn, may return this air to the cartridge 32 through a second port interface 154 to be received within a reaction chamber of the cartridge 32 being of the designs described above with respect to FIG. 2 or FIG. 3. The reaction chamber outflow may pass through a third port interface 156 back into the housing 20 to be received by the sensor chamber 60 described as above, ultimately to be communicated to connector 24 and from there to the respiratory appliance 14 (not shown).

In this embodiment, the cartridge 32 may also include a scrubber element 160 receiving excess carbon monoxide through connector 150 from return line 142 to reduce carbon monoxide discharged into the atmosphere. In this design, the consumable filter 42 and scrubber element 160 may thus be replaced with the cartridge 32 to ensure their freshness.

In order to promote portability in the movement of organ carrier system 120 for transporting the organ 130, a battery pack 162 may be included within the housing 20 which provides for short-term energy storage necessary for organ transportation.

It will be generally appreciated that the fan 40 may be located either upstream or downstream from the reaction chamber provided by the cartridge 32. Generally, the fan is not limited to propeller type designs but may be any kind of air pump including blowers, bellows, ionic pumps and the like. Other sources of heat beyond the laser and filament are also contemplated including non-coherent light sources such as flash tubes or LED arrays, or microwave and radiofrequency energy, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a processor, can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. An organ transplant container system comprising:
    an insulated container for receiving a transplant organ held in a storage liquid;
    a carbon monoxide generator assembly attached to the insulated container and communicating with the storage liquid to provide a source of carbon monoxide to the storage liquid by heating a solid state carbon source in atmospheric pressure air wherein the carbon monoxide generator assembly provides a releasably connectable cartridge including a reaction chamber holding the solid state carbon source communicating with the storage liquid; and
    a scrubber element communicating with the storage liquid to vent gas from the storage liquid into the scrubber element and to scrub carbon monoxide from the vented gas.

2. The organ transplant container system of claim 1 wherein the carbon monoxide generator provides:
    a reaction chamber holding a purified carbon element and providing an ingress port and egress port;
    a pump communicating with the ingress port to provide a source of air passing into the reaction chamber and out of the egress port;
    an electrically controllable heater element heating the purified carbon element to generate carbon monoxide gas from the reaction of the heated purified carbon with the air of the reaction chamber; and
    a respiratory delivery appliance communicating with the egress port to provide carbon monoxide to the insulated container.

3. The organ transplant container system of claim 2 wherein the purified carbon element is at least USP grade pure carbon.

4. The organ transplant container system of claim 2 wherein the electrically controllable heater element is an ohmic resistor in thermal communication with the purified carbon element.

5. The organ transplant container system of claim 2 wherein the electrically controllable heater element is an optical radiation source focused on the purified carbon element.

6. The organ transplant container system of claim 5 wherein the optical radiation source is a solid-state laser.

7. The organ transplant container system of claim 2 further including
    a sensor system for monitoring carbon monoxide passing through the egress port; and
    an electronic controller receiving a signal from the sensor system to control the electrically controllable heater in response thereto.

8. The medical carbon monoxide generator of claim 7 wherein the electronic controller controls the electrically controllable heater element to provide a predetermined time varying change in carbon monoxide delivered to the respiratory delivery appliance.

9. The medical carbon monoxide generator of claim 7 wherein the electronic controller further records a time record of carbon monoxide delivery through the egress port.

10. The medical carbon monoxide generator of claim 7 wherein the electronic controller determines a total amount of carbon monoxide generated in the reaction chamber during operation of the medical carbon monoxide generator.

11. The medical carbon monoxide generator of claim 7 further including redundant carbon monoxide sensors and wherein the electronic controller uses readings from the carbon monoxide sensors to deduce carbon monoxide concentration in the egress port.

12. The medical carbon monoxide generator of claim 1 wherein the cartridge includes a data communication element communicating with a remainder of the medical carbon monoxide generator system to identify the cartridge for controlling operation of the medical carbon monoxide generator.

13. The medical carbon monoxide generator of claim 12 wherein the electrically controllable heater according to the identification of the cartridge provides at least one of a predetermined schedule of carbon monoxide delivery from the cartridge and a predetermined total production of carbon monoxide from the cartridge.

14. The medical carbon monoxide generator of claim 12 wherein the data communication element includes a memory for storing usage data with respect to the reaction chamber.

15. The medical carbon monoxide generator of claim 2 further including a filter filtering the air received by the pump.

16. The organ transplant container system of claim 1 further comprising:

a delivery line holding a diffusion element providing for an introduction of carbon monoxide gas through the storage liquid; and a return line holding a liquid filter resisting flow of liquid from the insulated container into the replaceable cartridge.

* * * * *